US009399005B2

(12) United States Patent
Valkonen et al.

(10) Patent No.: US 9,399,005 B2
(45) Date of Patent: Jul. 26, 2016

(54) NAIL POLISH REMOVER COMPOSITION AND ITS USE

(75) Inventors: Jan Valkonen, Joensuu (FI); Martti Kivioja, Turku (FI)

(73) Assignee: OY FAINTEND LTD, Salo (FI)

( * ) Notice: Subject to any disclaimer, the term of this patent is extended or adjusted under 35 U.S.C. 154(b) by 0 days.

(21) Appl. No.: 14/006,363

(22) PCT Filed: Mar. 21, 2012
(Under 37 CFR 1.47)

(86) PCT No.: PCT/FI2012/050281
§ 371 (c)(1),
(2), (4) Date: Apr. 15, 2014

(87) PCT Pub. No.: WO2012/127113
PCT Pub. Date: Sep. 27, 2012

(65) Prior Publication Data
US 2014/0309153 A1 Oct. 16, 2014

(30) Foreign Application Priority Data
Mar. 22, 2011 (FI) ..................................... 20115276

(51) Int. Cl.
| | |
|---|---|
| *C11D 1/12* | (2006.01) |
| *C11D 3/43* | (2006.01) |
| *C11D 3/44* | (2006.01) |
| *A61K 8/33* | (2006.01) |
| *C11D 3/20* | (2006.01) |
| *C11D 3/34* | (2006.01) |
| *C11D 1/14* | (2006.01) |
| *A61K 8/34* | (2006.01) |
| *A61Q 3/04* | (2006.01) |
| *A61K 8/39* | (2006.01) |
| *A61K 8/46* | (2006.01) |

(52) U.S. Cl.
CPC ... *A61K 8/33* (2013.01); *A61K 8/34* (2013.01); *A61K 8/39* (2013.01); *A61K 8/466* (2013.01); *A61Q 3/04* (2013.01); *C11D 1/12* (2013.01); *C11D 1/14* (2013.01); *C11D 3/201* (2013.01); *C11D 3/2003* (2013.01); *C11D 3/2006* (2013.01); *C11D 3/2041* (2013.01); *C11D 3/2068* (2013.01); *C11D 3/3409* (2013.01); *A61K 2800/30* (2013.01)

(58) Field of Classification Search
CPC .......... C11D 1/12; C11D 1/14; C11D 3/2003; C11D 3/2006; C11D 3/201; C11D 3/2041; C11D 3/2068; C11D 3/3409

USPC ................. 510/118, 238, 432, 492, 505, 506
See application file for complete search history.

(56) References Cited

U.S. PATENT DOCUMENTS

| | | | |
|---|---|---|---|
| 2,197,630 A | 4/1940 | Carter | |
| 2,268,642 A | 1/1942 | Carter | |
| 5,744,437 A * | 4/1998 | Rowe et al. | ................... 510/204 |
| 5,981,453 A | 11/1999 | Faingold | |
| 6,028,040 A * | 2/2000 | Jarema | ......................... 510/118 |
| 2004/0038847 A1* | 2/2004 | Gross | ................. C11D 17/0021 510/424 |
| 2004/0058833 A1* | 3/2004 | Gross | ..................... C09D 9/005 510/201 |
| 2005/0130869 A1* | 6/2005 | Gross | ...................... C11D 1/83 510/473 |
| 2005/0233925 A1* | 10/2005 | Foley et al. | .................... 510/197 |
| 2006/0216250 A1* | 9/2006 | Schultz | .................... A61K 8/88 424/59 |
| 2008/0009429 A1 | 1/2008 | Klug et al. | |
| 2010/0056415 A1* | 3/2010 | Rong et al. | .................... 510/238 |
| 2010/0206328 A1* | 8/2010 | Dreilinger et al. | ................. 134/6 |
| 2010/0240752 A1* | 9/2010 | Dreilinger et al. | ............ 514/557 |
| 2010/0317560 A1* | 12/2010 | Ryther et al. | ................ 510/218 |
| 2011/0105377 A1* | 5/2011 | Yianakopoulos et al. | ..... 510/365 |
| 2011/0160116 A1* | 6/2011 | Mckechnie et al. | .......... 510/362 |
| 2011/0229424 A1* | 9/2011 | Schumann | ............... A61K 8/06 424/62 |
| 2011/0230385 A1* | 9/2011 | Murphy et al. | ................ 510/382 |
| 2012/0010118 A1* | 1/2012 | Ishizuka et al. | ................ 510/329 |
| 2012/0231989 A1* | 9/2012 | Murphy et al. | ................ 510/382 |

FOREIGN PATENT DOCUMENTS

| | | |
|---|---|---|
| DE | 38 37 985 A1 | 5/1990 |
| FI | 91274 C | 11/1995 |
| WO | WO 90/01313 A1 | 2/1990 |
| WO | WO00/52128 * | 9/2000 |

OTHER PUBLICATIONS

International Search Report and Written Opinion dated Jun. 28, 2012 issued in PCT/FI2012/050281.
European Search Report dated Aug. 13, 2014 issued in corresponding European Patent Application No. EP 12 76 0299.

* cited by examiner

*Primary Examiner* — Gregory R Delcotto
(74) *Attorney, Agent, or Firm* — Scully Scott Murphy and Presser

(57) ABSTRACT

The present invention relates to a water based nail polish remover composition comprising an anionic surfactant, a water soluble solvent, and water; wherein the anionic surfactant is selected from the group consisting of secondary $C_6$-$C_{22}$-alkane sulfonate trialcohol amine salts and mixtures thereof. The invention also relates to the use of the composition for removing nail polish.

18 Claims, No Drawings

NAIL POLISH REMOVER COMPOSITION AND ITS USE

FIELD OF THE INVENTION

The present invention relates removal of nail polish and in particular to a nail polish remover composition and its use for removing nail polish.

BACKGROUND OF THE INVENTION

Conventionally nail polish removers contain organic solvents, such as acetone, alkyl acetate, acetonitrile or combinations thereof, as active ingredients. These solvents have undesired properties including volatility and flammability, and they are highly toxic and extremely malodorous. They can also be harmful, irritating, drying, and damaging to the skin and nails when used as nail polish removers. Known nail polish removers are often allergenic and there are no or few non-allergenic nail polish removers available. Furthermore, nail polish removers containing said abovementioned organic solvents used in connection of artificial nails, such as acrylic, gel, or silk, linen or fibreglass wraps can weaken or dissolve the resins or sculpting products used to form or bond them to the natural nail or both.

A benign nail polish remover based on ethyl lactate, a biodegradable compound with low toxicity, is described in WO9416671. This compound, however, has a low flash point of only 46° C. and is irritating to respiratory system and may inflict serious damage to the eyes. Various agents for removing nail polish have also been described in U.S. Pat. No. 2,268,642 A, U.S. Pat. No. 2,197,630 A and US 2004038847 A1.

BRIEF DESCRIPTION OF THE INVENTION

It is thus an object of the present invention so as to overcome the above problems to provide a non-toxic and/or environmentally benign nail polish remover free from acetone, alkyl acetate, acetonitrile or combinations thereof. A further object is to provide a nail polish remover that is less or non-inflammable. Yet another object of the present invention is to provide a nail polish remover that is less or non-allergenic. The objects of the invention are achieved by a water based nail polish remover composition and its use for removing nail polish, both of which are characterized by what is stated in the relating independent claims. The preferred embodiments of the invention are disclosed in the dependent claims.

The prior art generally fails to provide a nail polish remover that is effective for removing nail polish and being non-malodorous, environmentally benign, less or non-toxic and benign to nails and skin. Accordingly, applicants have developed a novel nail polish remover composition comprising water, water soluble solvent and surfactant. The invention is based on the surprising realization that addition of an effective amount of surfactant to a nail polish remover composition comprising water soluble solvent and water renders it effective for the efficient removal of nail polish from natural and artificial nails.

An advantageous feature of the nail polish remover composition of the present invention is reduced level of toxicity and/or enhanced biodegradability due to the nature of the comprised benign constituents. Another advantageous feature of the nail polish remover composition of the present invention and its use is that it is less or non-malodorous or less harmful to the skin and the nails or both as compared to conventional nail polish removers. Furthermore, in accordance to one aspect of the present invention the nail polish remover composition is potentially non-allergenic. The nail polish remover in accordance of the present invention is free of acetone, alkyl acetate, acetonitrile or combinations thereof.

DETAILED DESCRIPTION OF THE INVENTION

According to the present invention there is provided a nail polish remover composition comprising an anionic surfactant, a water soluble solvent and water, wherein anionic surfactant is selected from the group consisting of secondary $C_6$-$C_{22}$-alkane sulfonate trialcohol amine salts and mixtures thereof.

The term "surfactant" herein refers to compounds that lower the surface tension of a liquid, allowing easier spreading and lowering the interfacial tension between a liquid and a solid or two liquids and comprise a hydrophilic head and a hydrophobic tail connected to the head. According to the present invention the surfactant is an anionic surfactant. The anionic surfactants used in the composition according to the present invention are trialcohol amine salts of secondary alkane sulfonates (SAS), also called paraffine sulfonates.

The SAS are secondary $C_6$-$C_{22}$-alkane sulfonates, more preferably $C_{10}$-$C_{20}$-alkane sulfonates, most preferably $C_{14}$-$C_{17}$-alkane sulfonates. Corresponding salts are formed with trialcohol amine, more preferably triethanol amine (TEA). In a preferred embodiment of the present invention the surfactant is a secondary $C_6$-$C_{22}$-alkane sulfonate triethanol amine salt, more preferably $C_{10}$-$C_{20}$-alkane sulfonate triethanol amine salt, most preferably a secondary $C_{14}$-$C_{17}$-alkane sulfonate triethanol amine salt. The composition of the present invention may comprise one or more surfactant(s), independently selected from the aforementioned surfactants. In accordance to the present invention the surfactant is present in an amount from 0.05 to 10% w/w (weight/total weight of the composition), preferably from 1 to 5% w/w.

The term "water soluble solvent" refers to solvents capable mixing with water fully i.e. in all proportions, or partly i.e. in some proportions. According to the present invention the water soluble solvent is preferably a glycol ether or; more preferably, a $C_2$-$C_8$-alkylene or di-$C_2$-$C_8$-alkylene glycol, or a $C_1$-$C_6$-alkyl ether thereof; or a mixture thereof. The term "$C_2$-$C_8$-alkylene glycol" herein refers to compounds having a $C_2$-$C_8$-alkyl carbon backbone and two hydroxyl groups each being attached to one available carbon atom. The said two carbon atoms are preferably adjacent. The $C_2$-$C_8$-alkyl group may be unbranched or branched. The term "di-$C_2$-$C_8$-alkylene glycol" refers to dimers of $C_2$-$C_8$-alkylene glycol groups joined together via an oxygen atom. Such a compound may consist of a mixture of possible isomeric compounds. The water soluble solvent of the present invention is preferably non-allergenic. Examples of preferred water soluble solvents include diethylene glycol ethers, dipropylene glycol ethers, hexylene glycol, and a mixture thereof. Especially preferred water soluble solvent is 2-(2-butoxyetoxy)ethanol (butoxydiglycol).

Water soluble solvent may be present in an amount from 5 to 95% w/w. In one aspect of the present invention water soluble solvent is present in an amount from 60 to 95% w/w, preferably from 80 to 95% w/w. In alternative aspect of the present invention water soluble solvent is present in an amounts form 5 to 30% w/w, preferably from 5 to 15% w/w.

In accordance to the present invention water may be present in the nail polish remover composition in an amount from 5 to 50% w/w, preferably from 5 to 30% w/w.

In accordance to one aspect of the present invention the nail remover composition is non-inflammable in temperatures under 220° C., preferably under 160° C., more preferably under 120° C., most preferably under 100° C.

The term "comprise" as used herein and hereafter describes the constituents of the nail polish remover composition of the present invention in a non-limiting manner i.e. the said nail polish remover comprising constituents consists of, at least, the said constituents, but may additionally, when desired, comprise other constituents. However, the said nail polish remover composition of the present invention comprising said constituents may consist of only the said constituents. The term "comprise" is further used to reflect that the composition of the present invention may comprise trace components of other materials or other impurities, or both, which do not alter the effectiveness or the safety of the mixture.

In accordance to one aspect of the present invention, the water soluble solvent is present in the nail polish remover composition in an amount from 5 to 95% w/w, water in an amount from 5 to 30% w/w, and surfactant in an amount from 0.05 to 10% w/w. In a preferred aspect of the present invention the water soluble solvent is present in an amount from 80 to 95% w/w, water in an amount from 5 to 20% w/w and surfactants in an amount from 0.05 to 5% w/w.

The nail polish remover composition of the present invention may optionally further comprise as a co-solvent one or more $C_1$-$C_{10}$-alcohol(s), which may optionally be substituted with one or two $C_1$-$C_3$-alkoxy group(s), preferably with one methoxy group. "$C_1$-$C_{10}$-alcohol" refers to alcohols comprising a $C_{1-10}$-alkyl group, preferably a $C_3$-$C_6$-alkyl group, and optionally attached OH-group, such as, for example, methanol, ethanol, n-propanol, i-propanol, n-butanol, i-butanol, t-butanol, n-pentanol, etc. The $C_1$-$C_{10}$-alkyl group may be un-branched or branched. The $C_{1-10}$-alcohol may be further substituted with one or more, preferably one, $C_1$-$C_3$ alkoxy group(s), preferably methoxy group(s), to render alcohols such as, for example, 1-methoxy-1-ethanol, 2-methoxy-1-ethanol 1-methoxy-2-propanol, 2-methoxy-1-propanol, 2-methoxy-2-propanol, etc. In one embodiment of the present invention the nail polish remover composition comprises 1-methoxy-2-propanol.

In accordance with one aspect of the present invention, the above described $C_1$-$C_{10}$-alcohol is present in the nail polish remover composition in an amount from 40 to 75% w/w, preferably from 60 to 70% w/w.

In accordance to an alternative preferred aspect of the present invention the water soluble solvent is present in an amount from 5 to 15% w/w, alcohol co-solvent in an amount from 60 to 70% w/w, water in an amount from 15 to 30% w/w, and surfactant in an amount from 0.05 to 10% w/w.

The nail polish remover composition of the present invention may optionally further comprise additional components that enhance efficiency such as emulsifying agents. Examples of such compounds include triethanolamine sulfate, PEG-5 cocamide and mixtures thereof. Said composition may optionally comprise components that nourish and/or promote the wellbeing of nails and/or the tissue surrounding the nail, and mixtures thereof. Such components include emollients, humectants, fragrances, coloring agents, conditioning agents, and other suitable components know to a person skilled in the art. Further components that may be present include Vitamin E and oily solvents. Yet further components that may be present in the composition are any such components that proved beneficial attributes to the nail polish remover composition of the present invention. The said additional component(s) in accordance to the present invention is(are) present in the nail polish remover composition in an amount up to 10% w/w. In one aspect of the present invention triethanolamine sulfate or PEG-5 cocamide or a mixture thereof is present in the nail polish remover composition in an amount from 0 to 2% w/w, preferably from 0.5 to 1% w/w.

Further according to the present invention there is provided the use of the above defined nail polish remover composition for removing nail polish. In accordance to one aspect of the present invention there is provided the use of the above defined nail polish remover composition for removing nail polish from nail, wherein said nail is fingernail or toenail.

The term "nail polish" as used herein refers to materials used for providing a protective and/or visual coating on fingernails and toenails. Examples of such material include, but are not limited to, materials known as nail polish, nail lacquer, nail polish-lacquer, nail enamel, etc. It is understood that nail polish can be applied to surfaces other than nails, and thus the composition provided herein can be used to remove nail polish from any surface having nail polish applied thereon. For example the compositions provided herein can be used for removing nail polish from surfaces including, but not limited to, skin, hair, clothing, shoes, handbags, jewelry, furniture, tables, counters, seats, equipment, or other surfaces with nail polish applied thereon.

The following examples illustrate a nail polish remover compositions of the present invention.

EXAMPLE 1

Nail Polish Composition 1

63% 1-methoxy-2-propanol
20% w/w water
15% w/w butoxydiglycol
1% w/w secondary $C_{14}$-$C_{17}$-alkane sulfonate TEA salt
0.5% w/w TEA sulfate
0.5% w/w PEG-5 cocamide

EXAMPLE 2

Nail Polish Composition 2

88% w/w butoxydiglycol
10% w/w water
1% w/w secondary $C_{14}$-$C_{17}$-alkane sulfonate TEA salt
0.5% w/w TEA sulfate
0.5% w/w PEG-5 cocamide It will be obvious to a person skilled in the art that, as the technology advances, the inventive concept can be implemented in various ways. The invention and its embodiments are not limited to the examples described above but may vary within the scope of the claims.

The invention claimed is:

1. A nail polish remover composition consisting of an anionic surfactant, a water soluble solvent, water and optionally one or more $C_1$-$C_{10}$ alcohol(s), which may be unsubstituted or substituted with one or more $C_1$-$C_3$-alkoxy group(s); wherein the anionic surfactant is selected from the group consisting of secondary $C_6$-$C_{22}$-alkane sulfonate trialcohol amine salts and mixtures thereof, and wherein the water soluble solvent is a glycol ether; a $C_2$-$C_8$-alkylene or di-$C_2$-$C_8$-alkylene glycol, or a $C_1$-$C_6$-alkyl ether thereof; or a mixture thereof.

2. The nail polish remover composition according to claim 1, wherein the anionic surfactant is a secondary $C_{10}$-$C_{20}$-alkane sulfonate trialcohol amine salt.

3. The nail polish remover composition according to claim 1, wherein the anionic surfactant is a secondary $C_{14}$-$C_{17}$-alkane sulfonate triethanol amine salt.

4. The nail polish remover composition according to claim 1, wherein the anionic surfactant is present in an amount from 0.05 to 10% w/w.

5. The nail polish remover composition according to claim 1, wherein the water soluble solvent is diethylene glycol ether, dipropylene glycol ether, hexylene glycol, or a mixture thereof.

6. The nail polish remover composition according to claim 1, wherein the water soluble solvent is present in an amount from 5 to 95% w/w.

7. The nail polish remover composition according to claim 1, wherein the water is present in an amount from 5 to 50% w/w.

8. The nail polish remover composition according to claim 1, wherein the one or more $C_1$-$C_{10}$-alcohol(s), which may be unsubstituted or substituted with one or more $C_1$-$C_3$-alkoxy group(s) is present.

9. The nail polish remover composition according to claim 8, wherein the $C_1$-$C_{10}$-alcohol is 1-methoxy-2-propanol, 2-methoxy-1-propanol, 2-methoxy-2-propanol, or a mixture thereof.

10. The nail polish remover composition according to claim 8, wherein the $C_1$-$C_{10}$-alcohol is present in an amount from 40 to 75% w/w.

11. The nail polish remover composition according to claim 1, wherein the anionic surfactant is present in an amount from 1 to 5% w/w.

12. The nail polish remover composition according to claim 8, wherein said one or more $C_1$-$C_3$-alkoxy group(s) is methoxy group(s).

13. A method of removing nail polish from a surface on which it is present comprising applying to said surface the nail polish remover composition according to claim 1.

14. The method according to claim 13, wherein the anionic surfactant is a secondary $C_{10}$-$C_{20}$-alkane sulfonate trialcohol amine salt.

15. The method according to claim 13, wherein the anionic surfactant is present in an amount from 0.05 to 10% w/w.

16. The method according to claim 13, wherein the water soluble solvent is present in an amount from 5 to 95% w/w.

17. The method according to claim 13, wherein the water is present in an amount from 5 to 50% w/w.

18. The method according to claim 13, wherein the surface is a toenail or fingernail.

* * * * *